(12) United States Patent
Krasutsky et al.

(10) Patent No.: US 6,232,481 B1
(45) Date of Patent: May 15, 2001

(54) METHOD FOR MANUFACTURING BETULINIC ACID

(75) Inventors: Pavel A. Krasutsky; Robert M. Carlson; Vitaliy V. Nesterenko, all of Duluth, MN (US)

(73) Assignees: Regents of the University of Minnesota, Minneapolis, MN (US); Naturtek, LLC, Duluth, MN (US)

( * ) Notice: Subject to any disclaimer, the term of this patent is extended or adjusted under 35 U.S.C. 154(b) by 0 days.

(21) Appl. No.: 09/480,406

(22) Filed: Jan. 11, 2000

(51) Int. Cl.$^7$ .................................................. C11C 31/00

(52) U.S. Cl. ......................... 554/167; 552/502; 560/257

(58) Field of Search .................... 554/167; 560/257; 552/502

(56) References Cited

U.S. PATENT DOCUMENTS 5,804,575    9/1998    Pezzuto et al. .

*Primary Examiner*—Deborah D. Carr
(74) *Attorney, Agent, or Firm*—Schwegman, Lundberg, Woessner & Kluth P.A.

(57) ABSTRACT

The present invention provides a method for preparing betulin-3-acetate including alcoholyzing betulin 3,28-dibenzoate; a process for preparing betulin-3-acetate including: (1) acylating betulin to provide betulin 3,28-dibenzoate and (2) alcoholyzing betulin 3,28-dibenzoate to provide betulin-3-acetate; and a process for preparing betulinic acid including: (1) acylating betulin to provide betulin 3,28-dibenzoate; (2) alcoholyzing betulin 3,28-dibenzoate to provide betulin-3-acetate; (3) oxidizing betulin-3-acetate to provide betulinic aldehyde-3-acetate; (4) oxidizing betulinic aldehyde-3-acetate to provide betulinic acid-3-acetate; and (5) deprotecting betulinic acid-3-acetate to provide betulinic acid.

22 Claims, 1 Drawing Sheet

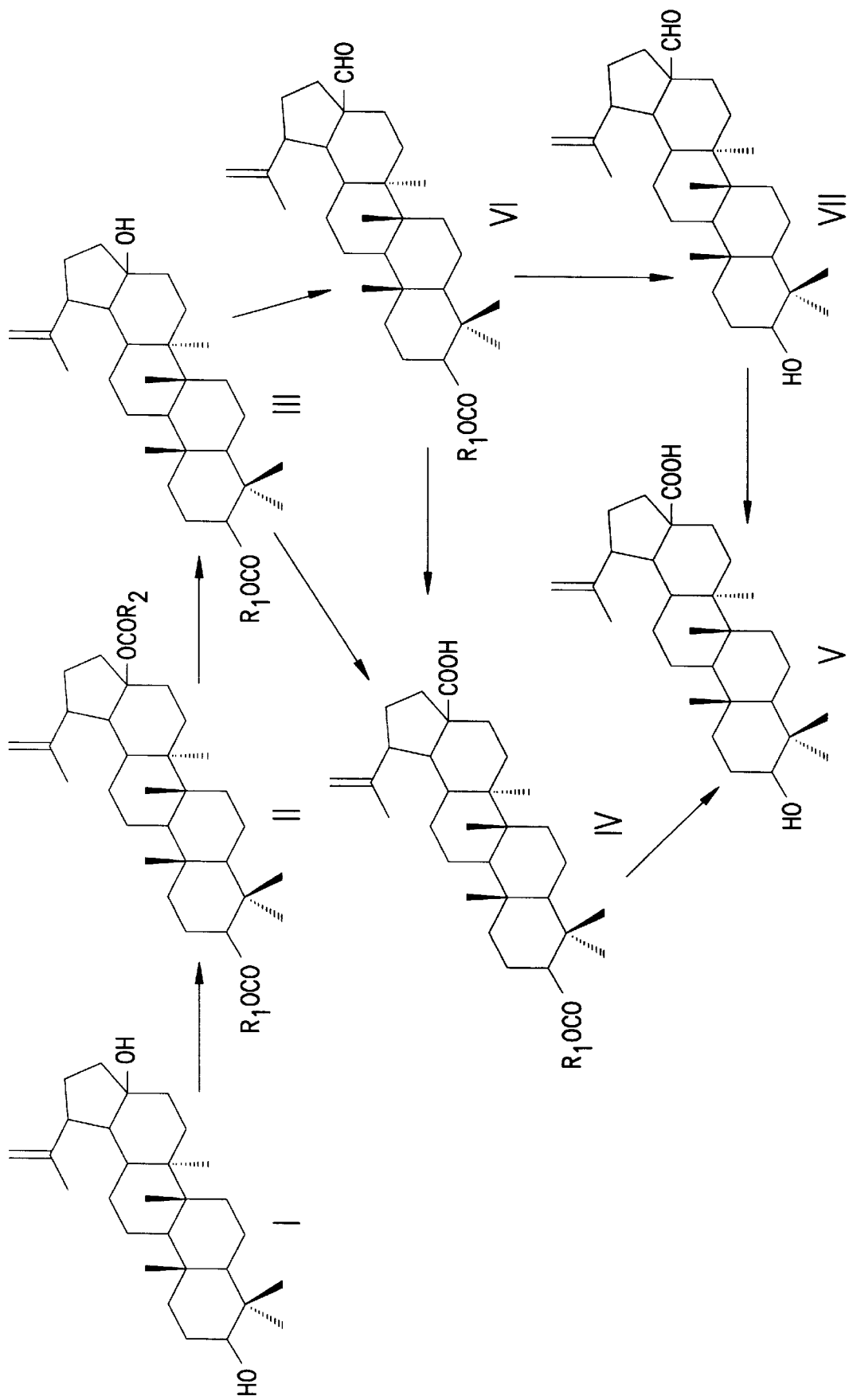

METHOD FOR MANUFACTURING BETULINIC ACID

BACKGROUND OF THE INVENTION

Betulinic acid is useful as a therapeutic agent. For example, Pisha, E. et al., (1995) *J. M. Nature Medicine*, 1, 1046–1051 disclose that betulinic acid has antitumor activity against melanoma, e.g., MEL-1, MEL-2 and MEL-4. In addition, Fujioka, T. et al., *J. Nat. Prod.*, (1994) 57, 243–247 discloses that betulinic acid has anti-HIV activity in H9 lymphocytic cells.

Betulinic acid can be manufactured from betulin, which is present in large quantities in the outer birch bark of numerous species of birch trees. For example, a single paper mill in northern Minnesota generates nearly 30–70 tons of birch bark per day. Approximately 230,000 tons of birch bark are generated per year. Outer bark of *Betula verrucosa* (European commercial birth tree) contains nearly 25% betulin (Rainer Ekman, 1983, Horzforschung 37, 205–211). The outer bark of *Betula paparifera* (commercial birch of northern U.S. and Canada) contains nearly 5–18% etulin (see, U.S. patent Ser. No. 09/371298). As such, vast quantities of betulin are available.

U.S. Pat. No. 5,804,575 issued to Pezzuto et al. discloses a five-step process for the synthesis of betulinic acid from betulin. Due to the length of time required to carry out this process and the yield it provides, it is not ideal for the commercial scale (e.g., kilogram) production of betulinic acid. Additionally, the process uses solvents and reagents that are hazardous and expensive, and the disclosed purification steps are not feasible on a commercial scale.

The first step in the preparation of betulinic acid from betulin-3-acetate was described by Ruzichka et al. (*Helv. Chim. Acta.*, 21, 1706–1715 (1938)).

The main obstacle for employing this method is the preparation of starting material (i.e., betulin-3-acetate). The selectivity of the hydrolysis of betulin-3, 28-diacetate with potassium hydroxide provided about 60% betulin-3-acetate. The use of magnesium alcoholates (Yao-Chang Xu et al., *J. Org. Chem.*, 61, 9086–9089 (1996)) in the selective deprotection of betulin-3,28-diacetate (Yao-Chang Xu et al., *J. Org. Chem.*, 61, 9086–9089 (1996)) has several serious drawbacks. The selectivity of this process is about 81%. Additionally, the cost of magnesium alcoholates is fairly high. As such, this method is not attractive for the commercial scale production of betulinic acid.

Thus, there exists a need for improved methods for preparing betulinic acid and synthetic precursors thereof. Such improved methods should require less time, should provide a higher overall yield, should be more cost effective (i.e., should require less expensive reagents and solvents) than known procedures, or should satisfy the contemporary industrial demands from both safety and environmental points of view.

SUMMARY OF THE INVENTION

The present invention provides a method for preparing betulinic acid and precursors thereof. The methods of the present invention require less time and require reagents that are less expensive, less toxic, or less flammable than known methods for preparing betulinic acid and the precursors thereof.

The present invention provides a process for preparing a compound of formula III

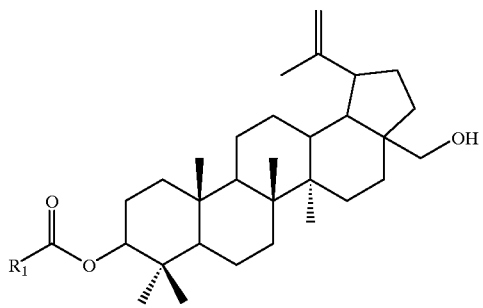

III comprising alcoholyzing a compound of formula II

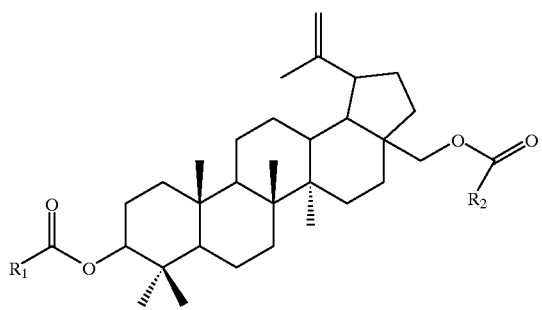

II wherein each $R_1$ and $R_2$ are each independently a suitable organic group.

The present invention also provides a process for preparing a compound of formula V

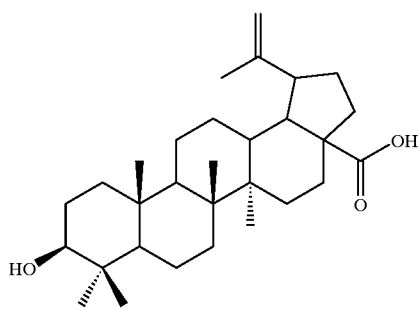

V comprising:

(1) acylating a compound of formula I

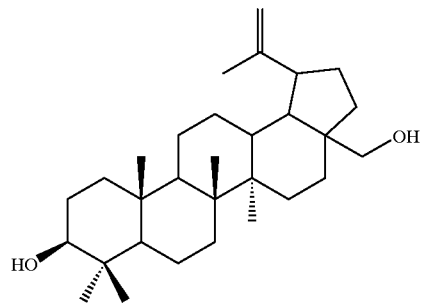

to provide a compound of formula II

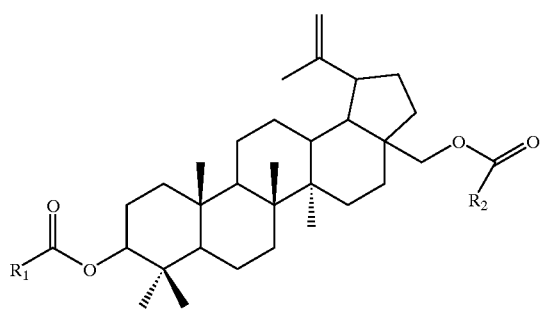

wherein each $R_1$ and $R_2$ are each independently a suitable organic group;

(2) alcoholyzing a compound of formula II to provide a compound of formula III;

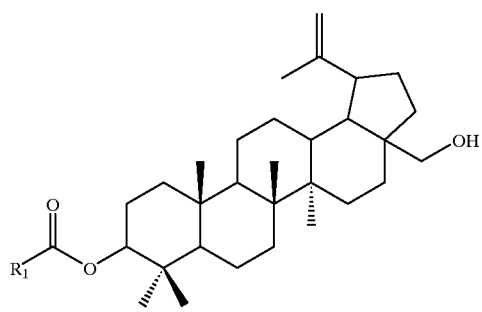

(3) oxidizing the compound of formula III to provide a compound of formula VI;

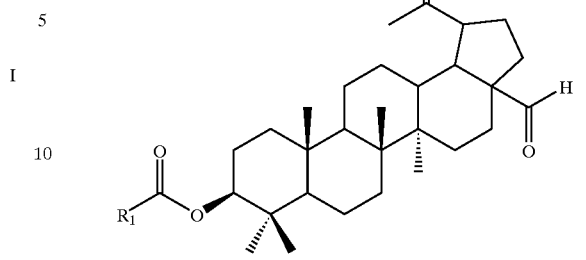

(4) oxidizing the compound of formula VI to provide a compound of formula IV; and

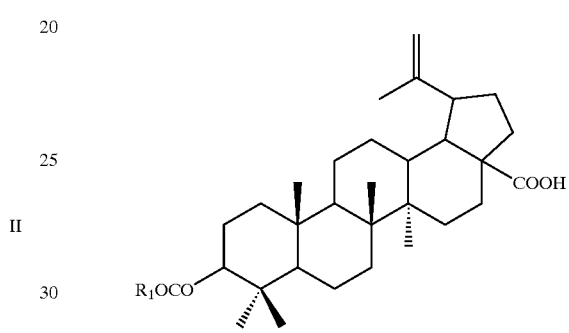

(5) deprotecting the compound of formula IV to provide the compound of formula V.

The invention also provides novel compounds disclosed herein, as well as methods for their synthesis.

BRIEF DESCRIPTION OF THE FIGURES

FIG. 1 is a schematic illustration of a synthesis of betulinic acid from betulin.

DETAILED DESCRIPTION OF THE INVENTION

As illustrated in FIG. 1 (scheme 1), Applicant has discovered a process for alcoholyzing the bisprotected alcohol (compound II) to provide the corresponding alcohol (compound III). The alcohol (compound III) can be oxidized to the acid (compound IV) and the acid (compound IV) can be deprotected to betulinic acid (compound V); or the alcohol (compound III) can be oxidized to the aldehyde (compound VI), the aldehyde (compound VI) can be oxidized to the acid (compound IV), and the acid (compound IV) can be deprotected to provide betulinic acid (compound V); or the alcohol (compound III) can be oxidized to the aldehyde (compound VI), the aldehyde (compound VI) can be deprotected to the aldehyde (compound VII), and the aldehyde (compound VII) can be oxidized to betulinic acid (compound V).

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

$(C_6-C_{10})$aryl denotes a phenyl radical or an ortho-fused bicyclic carbocyclic radical having about nine to ten ring atoms in which at least one ring is aromatic.

Specific and preferred values listed below for radicals, substituents, and ranges, are for illustration only; they do not exclude other defined values or other values within defined ranges for the radicals and substituents.

Specifically, $(C_1-C_{10})$alkyl can be methyl, ethyl, propyl, isopropyl, butyl, iso-butyl, sec-butyl, pentyl, 3-pentyl, hexyl, heptyl, octyl, nonyl or decyl;

$(C_1-C_{10})$alkoxy can be methoxy, ethoxy, propoxy, butoxy, iso-butoxy, sec-butoxy, pentoxy, 3-pentoxy, hexyloxy, heptyloxy, octyloxy, nonyloxy, or decyloxy;

$(C_2-C_{10})$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, or 9-decenyl;

$(C_2-C_{10})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-onynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, or 9-decynyl;

$(C_6-C_{10})$aryl can be phenyl, indenyl or naphthyl; and $(C_3-C_6)$cycloalkyl can be cyclopropyl, cyclobutyl, cyclopentyl, or cyclohexyl.

As illustrated in FIG. 1, the alcohol (compound I) can be acylated to provide the bisprotected alcohol (compound II). $R_1$ and $R_2$ can be any suitable organic group provided $R_2C(=O)$— can be selectively removed (e.g., alcoholyzed) in the presence of $R_1$. Suitable organic groups include $(C_1-C_{10})$alkyl, $(C_2-C_{10})$alkenyl, $(C_2-C_{10})$alkynyl, $(C_6-C_{10})$aryl, $(C_1-C_{10})$alkoxy or $(C_6-C_{10})$aryl$(C_1-C_{10})$alkyl, wherein any alkyl, alkoxy, alkenyl, alkynyl, aryl or arylalkyl of $R_1$ and $R_2$ can be optionally substituted with one or more halo, nitro, cyano, trifluoromethyl, hydroxy, SR or NRR, wherein each R is independently H or $(C_1-C_{10})$alkyl. Specifically, $R_1$ and $R_2$ can each independently be $(C_1-C_{10})$ alkyl, $(C_2-C_{10})$alkenyl, $(C_2-C_{10})$alkynyl, or $(C_6-C_{10})$aryl. More specifically, $R_1$ and $R_2$ can independently be $(C_1-C_{10})$ alkyl (e.g. methyl).

The acylation can be carried out employing any suitable acylating reagent (e.g., an acid anhydride, a carboxylic acid, or an acid chloride). Suitable acid anhydrides include acetic anhydride, benzoyl anhydride, maleic anhydride, phtalic anhydride, and succinic anhydride. Suitable carboxylic acids include acetic acid and benzoic acid. Suitable acid chlorides include acetyl chloride, pentanoyl chloride and benzoyl chloride. In addition, the acylation can be carried out employing any suitable alkyl acylate (e.g., alkyl acetate). Specifically, the acylating reagent can be acetic anhydride, acetyl chloride or acetic acid.

The acylation can be carried out at any suitable temperature that allows for the acylation of both the primary and secondary alcohols. Specifically, the reaction can be carried out at a temperature above about 25° C. or above about 70° C. More specifically, the reaction can be carried out at a temperature above about 100° C. or above about 118° C.

The acylation can be carried out in any suitable solvent. Suitable solvents include ethers, esters, acetone, methylene chloride, chloroform, carbon tetrachloride, THF, dicloromethane, pyridine, and aromatic solvents (e.g., benzene, xylenes, toluene, trifluoromethylbenzene, o-chlorotrifluoromethylbenzene, m-chlorotrifluoromethylbenzene, and p-chlorotrifluoromethylbenzene).

The acylation can be carried out for any suitable length of time. The length of time will vary and depends in part upon the nature and amount of reagents and solvents as well as the temperature of the reaction. Typically, the acylation can proceed for less than about 10 hours, less than about 7 hours, or less than about 3 hours.

Other suitable acylating reagents and reaction conditions are known in the art, for example see Greene, T. W.; Wutz, P. G. M., *Protecting Groups In Organic Synthesis*, second edition, 1991, New York, John Wiley & sons, Inc and Morrison, R. and Boyd, R., *Organic Chemistry*, 672–674, third edition, 1977, Boston, Allyn and Bacon.

The alcohol (compound I) can be acylated to the bisprotected alcohol (compound II) employing acetic anhydride/ acetic acid (i.e., $Ac_2O/AcOH$) in a yield greater than about greater than about 90%, greater than about 95%, or greater than about 99%. In addition, the acylation typically provides compound II (i.e., bis acylated compound) and the mono acylated compounds (the compound wherein the primary hydroxyl group is acylated and the secondary hydroxyl group remains unreacted and the compound wherein the secondary hydroxyl group is acylated and the primary hydroxyl group remains unreacted) in a ratio of about 90:10, and preferably in a ratio of at least about 95:5, or in a ratio of at least about 98:2.

As illustrated in FIG. 1, the bisprotected alcohol (compound II) can be alcoholyzed to provide the alcohol (compound III). As used herein, "alcoholize," includes removing a primary acyl group to provide a primary hydroxyl group, while a secondary acyl group present on the same compound is not removed to any appreciable degree. Accordingly, the alcoholysis of a compound containing both a primary acyl group and a secondary acyl group can provide a mixture of compounds (e.g., the compound wherein the primary acyl group, but not the secondary acyl group, is alcoholyzed; the compound wherein both the primary and secondary acyl groups are alcoholyzed; and the compound wherein the secondary acyl group, but not the primary acyl group, is alcoholyzed). The alcoholysis typically provides the compound wherein the primary acyl group, but not the secondary acyl group, is alcoholyzed and the compound wherein both the primary and secondary acyl groups are alcoholyzed, in a ratio of about 80:20, and preferably in a ratio of at least about 90:10, or in a ratio of at least about 95:5.

The alcoholysis can be carried out employing any suitable aluminum alkoxide (e.g., aluminum methoxide, aluminum ethoxide, aluminum isopropoxide, or aluminum butoxide). As used herein, "aluminum alkoxide" is $Al(O-R)_3$ wherein $R_3$ is $(C_1-C_{10})$alkyl, $(C_2-C_{10})$alkenyl, or $(C_2-C_{10})$alkynyl.

A specific aluminum alkoxide is aluminum methoxide $Al(OMe)_3$, aluminum ethoxide $Al(OEt)_3$, aluminum isopropoxide $Al(O-iso-propyl)_3$, aluminum n-propoxide $Al(O-n-propyl)_3$, aluminum sec-butoxide $Al(O-sec-butyl)_3$, or aluminum tert-butoxide $Al(O-tert-butyl)_3$. Specifically, aluminum alkoxide is aluminum isopropoxide $Al(O-iso-propyl)_3$, as illustrated in the Examples.

The alcoholysis can be carried out in any suitable solvent (e.g., an anhydrous alcohol). Particular alcohols for use in the present invention will typically have between about 1 and about 10 carbon atoms; can be cyclic or aliphatic; can be saturated or unsaturated; and can be branched or straight-chained. Specific alcohols suitable for use in the present invention include methanol, ethanol, tert-butanol, and iso-propanol. Specifically, the alcohol is iso-propanol, as illustrated in the Examples. More specifically, from an environmental or recycling point of view, the same alcohol from which the aluminum alkoxide was prepared can be employed. For example, if aluminum iso-propoxide is employed, isopropanol can be employed as a solvent for alcoholysis.

The alcoholysis can be carried out at any suitable temperature. Specifically, the alcoholysis can be carried out at a temperature above about 25° C. More specifically, the alcoholysis can be carried out at a temperature above about 50° C. or above about 75° C. (i.e., the boiling temperature of the solvent).

The alcoholysis can be carried out for any suitable length of time, provided the primary acyl group is selectively removed (i.e., the primary acyl group is removed to a greater degree than the secondary acyl group). Specifically, the alcoholysis can be carried out for about 0.5 to about 4 hours, for about 1 to about 3 hours, or about 1 to about 2 hours, as illustrated in the Examples.

Applicant has discovered that an aluminum alkoxide in an anhydrous alcohol will selectively cleave (i.e., selectively alcoholize) the primary acyl group of compound II in the presence of the secondary acyl group. Specifically, the alcoholysis typically provides compound III (i.e., product) and compound II (i.e., starting material) in a ratio of about 80:20, and preferably in a ratio of at least about 90:10, in a ratio of at least about 95:5 or in a ratio of at least 98:2. In addition, the alcoholysis typically provides compound III and the compound wherein both the primary acyl group and the secondary acyl group of compound II are alcoholyzed, in a ratio of about 80:20, and preferably in a ratio of at least about 90:10, in a ratio at least about 95:5, or in a ratio of at least 98:2.

As illustrated in figure I, the alcohol (compound III) can be oxidized to the aldehyde (compound VI). Applicant has discovered that the oxidation can be carried out employing oxalyl chloride (i.e., $(COCl)_2$) in dimethyl sulfoxide (i.e., DMSO) in methylene chloride (i.e., $CH_2Cl_2$). Specifically, the oxidation typically provides compound VI (i.e., product) and compound III (i.e., starting material) in a ratio of about 80:20, and preferably in a ratio of at least about 90:10, or in a ratio of at least about 95:5. In addition, the oxidation typically provides compound VI (i.e., product) in a yield of at least about 80%, and preferably at least about 85%, or at least about 95%, based on starting material (i.e., compound III). Specifically, the oxidation typically provides compound VI (i.e., product) in a yield of at least about 95% if no purification step is necessary.

Alternatively, the alcohol (compound III) can be oxidized to the aldehyde (compound VI) employing oxygen (i.e., $O_2$) on palladium acetate (i.e., $Pd(OAc)_2$), as illustrated in the Examples. Specifically, the oxidation typically provides compound VI (i.e., product) and compound III (i.e., starting material) in a ratio of about 80:20, and preferably in a ratio of at least about 90:10, or in a ratio of at least about 95:5. In addition, the oxidation typicaly provides compound VI (i.e., product) in a yield of about 70%, and typically at least about 80%, or at least about 85%, based on starting material (i.e., compound III).

The oxidation can be carried out at any suitable temperature, provided the alcohol is oxidized to the aldehyde and the secondary acyl group remains intact. Specifically, the oxidation can be carried out at a temperature below about −30° C., below about −40° C., or below about −50° C. More specifically, the oxidation can be carried out at a temperature between about −50° C. and about −60° C.

The oxidation can be carried out for any suitable length of time, provided the alcohol is oxidized to the aldehyde and the secondary acyl group remains intact. Specifically, the oxidation can be carried out for about 1 to about 5 hours, for about 1 to about 3 hours, or about 1 to about 2 hours, as illustrated in the Examples.

Other reagents suitable for oxidizing an alcohol to an aldehyde are known in the art, for example see Carey, F. & Sundberg, R., *Advanced Organic Chemistry*, 481–490, second edition, Vol. B, Plenum Press, New York and London and Morrison, R. and Boyd, R., *Organic Chemistry*, 520–587, third edition, 1977, Boston, Allyn and Bacon.

As illustrated in figure I, the aldehyde (compound VI) can be oxidized to the carboxylic acid (compound IV). The carboxylic acid (compound IV) can be isolated as the free acid, or can be isolated as a salt of the carboxylic acid. Specifically, the salt can be a pharmaceutically acceptable salt. Applicant has discovered that the oxidation can be carried out employing oxygen and NHPI (or ABIN or TEMPO) in trifluoromethylbenzene, which is commercially available as OXSOL 2000® from Occidental Chemical Corporation (Oxychem). As used herein, NHPI is N-hydroxyphthalimide. As used herein, "AIBN" is 2,2'-Azobisisobutyronitrile and is commercially available from Aldrich (Milwaukee, Wis.) and "TEMPO" is 2,2,6,6-tetramethyl-1-piperidinyloxy, fee radical and is commercially available from Aldrich (Milwaukee, Wis.). Specifically, the oxidation typically provides compound IV (i.e., product) and compound VI (i.e., starting material) in a ratio of about 80:20, and preferably in a ratio of at least about 90:10, or in a ratio of at least about 95:5. In addition, the oxidation typically provides compound IV (i.e., product) in a yield of about 65%, and preferably at least about 70%, or at least about 80%, based on starting material (i.e., compound VI).

Alternatively, the aldehyde (compound VI) can be oxidized to the carboxylic acid (compound IV) employing cobalt(III)acetylacetonate (i.e., $Co(AcAce)_3$) trifluoromethylbenzene, and oxygen, as illustrated in the Examples. Specifically, the oxidation typically provides compound IV (i.e., product) and compound VI (i.e., starting material) in a ratio of about 80:20, and preferably in a ratio of at least about 90:10, or in a ratio of at least about 95:5. In addition, the oxidation typically provides compound IV (i.e., product) in a yield of about 85%, and preferably at least about 90%, or at least about 95%, based on starting material (i.e., compound VI).

The oxidation can be carried out at any suitable temperature, provided the aldehyde is oxidized to the carboxylic acid and the secondary acyl group remains intact. Specifically, the oxidation can be carried out at a temperature between about 30° C. and about 70° C., between about 40° C. and about 60° C., or between about 45° C. and about 50° C.

The oxidation can be carried out for any suitable length of time, provided the aldehyde is oxidized to the carboxylic acid and the secondary acyl group remains intact. Specifically, the oxidation can be carried out for about 1 to about 10 hours, for about 4 to about 8 hours, about 5 to about 7 hours, or about 6 hours, as illustrated in the Examples.

Other suitable oxidative reagents and reaction conditions are known in the art, for example see Carey, F. & Sundberg, R., *Advanced Organic Chemistry*, 481–490, second edition, Vol. B, Plenum Press, New York and London and Morrison, R. and Boyd, R., *Organic Chemistry*, 520–587, third edition, 1977, Boston, Allyn and Bacon.

As illustrated in FIG. 1, the alcohol (compound III) can be oxidized directly to the carboxylic acid (compound IV). The carboxylic acid (compound IV) can be isolated as the free acid, or can be isolated as a salt of the carboxylic acid. Specifically, the salt can be a pharmaceutically acceptable salt. The oxidation can be carried out employing any suitable oxidative reagent (see, for example, March, *Advanced Organic Chemistry, Reactions, Mechanism and Structure*, 2nd Ed., McGraw Hill, 1977, pp. 1107–1108, and references cited therein). Suitable oxidative reagents include: 1) chromium (IV) oxide (i.e., $CrO_3$) and acetic acid (i.e., HOAc) (*J. Am. Chem. Soc.*, 78, 2255 (1956)); 2) chromium (IV) oxide (i.e., $CrO_3$) and sulfuric acid (i.e., $H_2SO_4$) (*J. Am. Chem. Soc.*, 48, 4404 (1983)); 3) potassium permanganate (i.e., $KMnO_4$) (*Tet. Lett.*, 28, 5263 (1987); *J. Am. Chem. Soc.*, 109, 7280 (1987)); 4) sodium manganate (i.e., $NaMnO_4$) (*Tet. Lett*, 22, 1655 (1981)); or 5) palladium chloride (i.e., $PdCl_2$), potassium carbonate (i.e., $K_2CO_3$) (*Chem. Lett.*, 1171 (1981)).

As illustrated in figure I, the acid (compound IV) can be deprotected to provide betulinic acid (compound V). Betulinic acid (compound V) can be isolated as the free acid, or can be isolated as a salt of betulinic acid (compound V). Specifically, the salt can be a pharmaceutically acceptable salt. Accordingly, the secondary acyl group can be removed.

Specifically, the deprotection can be carried out by hydrolysis. The deprotection (e.g., hydrolysis) can be carried out employing any suitable conditions (e.g., under acidic or basic conditions). Suitable acids include mineral acids (e.g., hydrochloric acid, nitric acid, sulfuric acid, and phosphoric acid). Suitable bases include metal hydroxides and carbonates (e.g., calcium carbonate and potassium carbonate). Suitable metal hydroxides include alkaline hydroxides (e.g., lithium hydroxide, sodium hydroxide and potassium hydroxide) and alkaline earth metal hydroxides (e.g., magnesium hydroxide and calcium hydroxide). Specifically, the hydrolysis can be carried out using sodium hydroxide in methanol, as illustrated in the Examples.

The deprotection (e.g., hydrolysis) can be carried out in any suitable solvent. Suitable solvents include an aqueous alcohol solution (i.e., alcohol and water) wherein alcohol is described hereinabove. In addition, the deprotection can be carried out at any suitable temperature that allows for the deprotection of the secondary acyl group. Specifically, the deprotection can be carried out at a temperature above about 25° C., above about 50° C. or above about 65° C. More specifically, the deprotection can be carried out at the boiling point of the solvent (e.g., if the solvent is methanol and water, the deprotection can be carried out at a temperature of about 105° C. to about 120° C).

The deprotection can be carried out for any suitable length of time. Specifically, the deprotection can be carried out for about 1 to about 24 hours, for about 1 to about 10 hours, or for about 1 to about 3 hours, as illustrated in the Examples.

Other suitable deprotection (e.g., hydrolysis) conditions are known in the art, for example see Carey, F. & Sundberg, R., *Advanced Organic Chemistry*, 481–490, second edition, Vol. B, Plenum Press, New York and London and Morrison, R. and Boyd, R., *Organic Chemistry*, 675–682, third edition, 1977, Boston, Allyn and Bacon.

Applicant has discovered a one-pot, synthetically viable, and cost-efficient method to prepare the alcohol (compound III) from betulin (compound I). The one-pot process is faster and less expensive than known methods. The monoprotected alcohol (compound III) can be oxidized to the acid (compound IV) which can be deprotected to betulinic acid (compound V). Alternatively, the monoprotected alcohol (compound III) can be oxidized to the aldehyde (compound VI), and the aldehyde (compound VI) can be oxidized to the acid (compound IV), and deprotected to betulinic acid (compound V). All of the procedures described herein above and illustrated in the Examples herein below can be scaled up to industrial scale (i.e., kilogram).

The present invention will be described by the following examples. The examples are for illustration purposes and do not otherwise limit the invention.

EXAMPLES

Betulin was obtained from outer birch bark employing the methods as disclosed in co-pending U.S. application Ser. No. 09/371,298; Elkman, R., (1983) Holzforsch, 37, 205; Ohara, S., et al., (1986) Mokuza Gakkaishi, 32, 266; and Eckerman, C., (1985) Paperi ja Puu, No. 3, 100.

Example 1

Betulin-3-acetate (III)

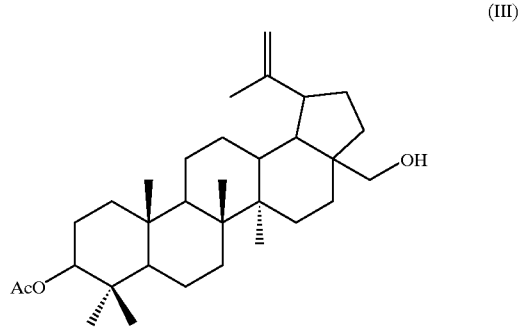

Acetic anhydride (85 ml) and acetic acid (800 ml) were introduced into round bottom flask (3 L). Betulin (I) (100 g, 0.2259 mol) was added to the stirred solution and refluxed for 3 hours. The reaction mixture was allowed to cool to 50° C. and acetic acid was evaporated under reduced pressure (25–30 mm Hg). Cream-white crystals of intermediate betulin-3,28-diacetate (II) were obtained after storage in vacuo (118.8 g, 0.2257 mol, 50–60° C., 0.1 mm Hg).

Isopropanol (i.e., i-PrOH) (2.5 L) and powdered aluminum iso-propoxide (i.e., $Al(O-i-Pr)_3$) (100 g, 0.223 mol) were added to the flask and the mixture was refluxed for 1.5 hours. Isopropyl alcohol was then removed under reduced pressure (100 mm Hg) at 30–33° C. The resulting white-orange crystals were dissolved in dichloromethane (1 L) and water (60 ml) was added to the solution. After stirring (10–15 minutes) the precipitated material was filtered, extracted with dichloromethane (4×200 ml) and dried over sodium sulfate (10 g). Solvent evaporation provided white crystals (m=105.21 g, 0.2171 mol, yield 96%, mp 256.4–263.6° C.). Crystallization from trifluoromethylbenzene yields 102.46 g (94% yield) of betulin 3-acetate (III): mp. 262.2–264° C.; IR (KBr) 3482, 2941, 2868, 1721, 1645, 1456, 1389, 1262, 1044, 888 cm$^{-1}$; $^1$H NMR (CDCl$_3$) δ 4.66 (S, 1H, 29-H), 4.55 (S, 1H, 29-H), 4.45 (DD, 1H, 3-H), 3.76 (D, 1H, 28-H), 3.29 (D, 1H, 28-H), 2.34 (M, 1H, 19-H), 2.03 (S, 3H, Ac-Me), 1.68 (S, 3H, 30-Me), 0.71, 0.76, 0.76, 0.92, 1.00, (all S, 5×3H, 27-, 23-, 24-, 25-, 26-Me), 1.01–2.4 (complex CH—, CH$_2$, 24 H,); $^{13}$C NMR (CDCl$_3$) δ 171.38, 150.75, 110.02, 81.22, 60.78, 55.63, 50.55, 48.99, 48.06, 48.06, 42.98, 41.19, 38.64, 38.07, 37.55, 37.34, 34.42, 34.25, 30.00, 29.42, 28.23, 27.30, 25.41, 23.97, 21.65, 21.11, 19.35, 18.46, 116.79, 16.47, 16.25.

Example 2
Betulinic aldehyde-3-acetate (VI)

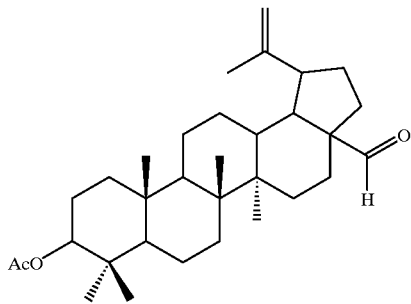

(VI)

Oxalyl chloride (15.72 g, 0.1237 mol) in methylene chloride (i.e., CH$_2$Cl$_2$) (500 ml) was placed in a round bottom two-neck flask (2 L). After cooling to −50 to −60° C. (dry ice bath) and with efficient stirring was added dimethylsulfoxide (i.e., DMSO) (12.87 g, 0.165 mol) in methylene chloride (500 ml) drop-wise over 5 to 10 minutes. The mixture was stirred for an additional 5 to 10 minutes (until gas evolution stops). Betulin-3-acetate (III) (powdered) (0.0825 mol, 40 g) was then added and allowed to stand for 45 minutes. After triethylamine (41.67 g, 0.4126 mol) was added, the cooling bath was removed and temperature allowed to increase to 10° C. Cold water (200 ml) was added and the mixture was extracted with methylene chloride (3×100 ml). The combined organic extracts were washed with water (5×100 ml), 5% HCl (2×100 ml) and brine (2×100 ml). After drying over sodium sulfate (10 g), evaporation of the solvent gave crude compound (39.6 g), which after crystallization from hexane gave white crystalline product, betulinic aldehyde-3-acetate (VI) (36.86 g, 93% yield) mp. 174.4–176.9° C., IR (KBr) 3069, 2942, 2865, 1727, 1641, 1447, 1376, 1245, 1028, 978, 883 cm$^{-1}$; $^1$H NMR (CDCl$_3$) δ 9.62 (S, 1 H, 28-H aldehyde), 4.69 (S, 1 H, 29-H), 4.57 (S, 1 H, 29-H), 4.21 (DD, 1 H, 3-H), 2.81 (M, 1 H, 19-H), 2.01 (S, 3 H, Me-OAc), 1.63 (S, 3 H, 30-Me), 0.82, 0.82, 0.82, 0.94, 0.96 (all S, 5×3 H, 23-, 24-, 25-, 26-, 27-Me), 1.05–2.1 (complex CH—, CH$_2$ 25 H); $^{13}$C NMR (CDCl$_3$) δ 207.01, 171.35, 149.995, 110.52, 81.19, 59.64, 55.67, 50.65, 48.3, 47.84, 42.84, 41.12, 38.96, 38.69, 38.08, 37.37, 34.53, 33.52, 30.13, 29.51, 29.09, 28.24, 25.76, 23.98, 21.65, 21.05, 19.28, 18.45, 16.79, 16.52, 16.19, 14.53; MS (E1) 482, 466, 454, 438, 422, 407, 393, 379, 262, 232, 217, 207, 189, 175, 161, 147, 135.

Example 3
Betulinic aldehyde-3-acetate (VI)

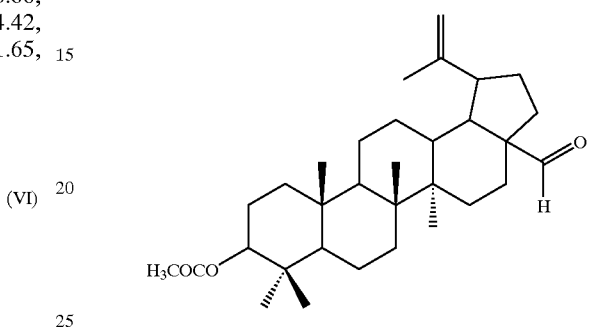

VI

Oxalyl chloride (7.86 g, 62 mmol) in trifluoromethylbenzene (250 ml) was placed in a round bottom two-neck flask (2 L). After cooling to −30 to 35° C. (i-PrOH-dry ice bath) and with efficient stirring was added dimethylsulfoxide (6.44 g, 83 mmol) in trifluoromethylbenzene (250 ml) drop-wise over 5 to 10 minutes. The mixture was stirred for an additional 5–10 minutes (until gas evolution stops). Powdered 3-O-acetyl-betulin (III) (40 g, 41 mmol) was then added. The resulting mixture was allowed to stand for 45 minutes. After triethylamine (41.67 g, 206 mmol) was added, the cooling bath was removed and the temperature was allowed to increase to 10° C. Cold water (100 ml) was added and the mixture was extracted with trifluoromethylbenzene (3×50 ml). The combined organic extracts were washed with water (5×50 ml), 5% HCl (2×50 ml) with brine (2×50 ml). After drying over sodium sulfate (5 g), evaporation of the solvent gave crude compound (19.3 g), which after crystallization from hexane gave white crystalline product (18.1 g, 91% yield), betulinic aldehyde-3-acetate (VI). mp. 174.5–176.8° C., IR (KBr) 3069, 2942, 2865, 1727, 1641, 1447, 1376, 1245, 1028, 978, 883 cm$^{-1}$; $^1$H NMR (CDCl$_3$) δ 9.62 (S, 1 H, 28-H aldehyde), 4.69 (S, 1 H, 29-H), 4.57 (S, 1 H, 29-H), 4.21 (DD, 1 H, 3-H), 2.81 (M, 1 H, 19-H), 2.01 (S, 3 H, Me-OAc), 1.63 (S, 3 H, 30-Me), 0.82, 0.82, 0.82, 0.94, 0.96, (all S, 5×3 H, 23-, 24-, 25-, 26-, 27-Me), 1.05–2.1 (complex CH—, CH$_2$ 25H); $^{13}$C NMR (CDCl$_3$) δ 207.01, 171.35, 49.995, 110.52, 81.19, 59.64, 55.67, 50.65, 48.3, 47.84, 42.84, 41.12, 38.96, 38.69, 38.08, 37.37, 34.53, 33.52, 30.13, 29.51, 29.09, 28.24, 25.76, 23.98, 21.65, 21.05, 19.28, 1845, 16.79, 16.52, 16.19, 14.53; MS (E1) 482, 466, 454, 438, 422, 407, 393, 379, 262, 232, 217, 207, 189, 175, 161, 147, 135.

Example 4
Betulinic aldehyde-3-acetate (VI)

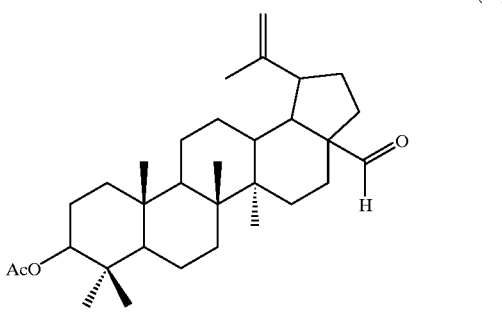

Palladium acetate (i.e., Pd(OAc)$_2$) (112 mg, 0.5 mmol) in trifluoromethylbenzene (500 ml) was introduced into a round bottom two neck flask (IL). Pyridine (158 mg, 2 mmol) and MS3A (i.e., molecular sieves, 3 Å) (5 g) were then added. The mixture was heated to 80 to 85° C. and oxygen was purged for 10 minutes. Betulin-3-acetate (III) (powdered) (4.84 g, 10 mmol) was added and oxygen was passed through the system at 80 to 85° C. for 1.5 hours. The mixture was filtered through silica gel (25 g, 230–400 mesh) to remove the catalyst. Evaporation of the solvent in vacuo gave crude product (4.8 g), which after crystallization from hexane yielded white crystals (4.12 g, 85%) of betulinic aldehyde-3-acetate (VI) mp. 174.5–176.8° C., IR (KBr) 3069, 2942, 2865, 1727, 1641, 1447, 1376, 1245, 1028, 978, 883 cm$^{-1}$; $^1$H NMR (CDCl$_3$) δ 9.62 (S, 1 H, 28-H aldehyde), 4.69 (S, 1 H, 29-H), 4.57 (S, 1 H, 29-H), 4.21 (DD, 1 H, 3-H), 2.81 (M, 1 H, 19-H), 2.01 (S, 3 H, Me-OAc), 1.63 (S, 3 H, 30-Me), 0.82, 0.82, 0.82, 0.94, 0.96 (all S, 5×3 H, 23-, 24-, 25-, 26-, 27-Me), 1.05–2.1 (complex CH—, CH$_2$ 25 H); $^{13}$C NMR (CDCl$_3$) δ 207.01, 171.35, 149.995, 110.52, 81.19, 59.64, 55.67, 50.65, 48.3, 47.84, 42.84, 41.12, 38.96, 38.69, 38.08, 37.37, 34.53, 33.52, 30.13, 29.51, 29.09, 28.24, 25.76, 23.98, 21.65, 21.05, 19.28, 18.45, 16.79, 16.52, 16.19, 14.53; MS (E1) 482, 466, 454, 438, 422, 407, 393, 379, 262, 232, 217, 207, 189, 175, 161, 147, 135.

Example 5
Betulinic acid-3-acetate (IV)

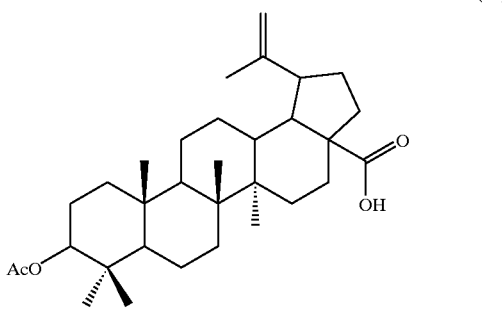

Betulinic aldehyde-3-acetate (VI) (3 g, 62.15 mmol) was dissolved in trifluoromethylbenzene (120 ml) and then was placed into a two-neck round bottom flask (250 ml). Methanol (1.2 ml) and NHPI (53 mg, 0.32 mmol) was added to the solution. Oxygen was bubbled through the solution at 15 to 20° C. for 2 hours. The reaction mixture was poured into cold water (50 ml) and extracted with trifluoromethylbenzene (2×20 ml). The combined organic fractions were washed with 1% aqueous solution of sodium bicarbonate until the water layer was colorless (4×30 ml). The trifluoromethylbenzene solution was dried over sodium sulfate (0.5 g) and the solvent evaporated in vacuo at 27 to 30° C. to give the crude product. Crystallization from MeOH-hexane gave white crystals (2.14 g 69%) of betulinic acid-3-acetate (IV): IR (KBr) 2938, 2867, 1741, 1692, 1640, 1450, 1372, 1231, 1184, 1046, 886, 775 cm$^{-1}$; $^1$H NMR (CDCl$_3$), δ 4.78 (S, 1 H, 29 H), 4.65 (S, 1 H, 29H), 4.54 (DD, 1H, 3-H), 3.02 (T, 1 H, 19 H), 2.097 (S, 3 H, Me-Ac), 1.69 (S, 3 H, 30-Me), 1.05–2.24 (complex CH—, CH$_2$ 25H); $^{13}$C NMR (CDCl$_3$) δ 180.403, 171.34, 150.44, 110.01, 81.24, 56.41, 55.471, 50.64, 49.42, 47.03, 42.59, 40.82, 39.01, 38.84, 38.53, 37.36, 37.19, 34.46, 32.29, 30.69, 29.85, 28.14, 27.54, 25.63, 21.65, 20.982, 19.518, 18.43, 16.28, 16.17, 15.51, 14.94; MS (E1) of Me-ester: 512, 497, 452, 437, 409, 393, 262, 249, 233, 215, 203, 189, 175, 161147, 133, 119, 107, 93, 81,69, 55,43.

Alternatively 3-acetyl-betulinic acid (IV) can be separated through the methyl ester by purification on silic (230–400 mesh, hexane:ether=3:1), m=2.58 (yield 81%).

Example 6
Betulinic acid (V)

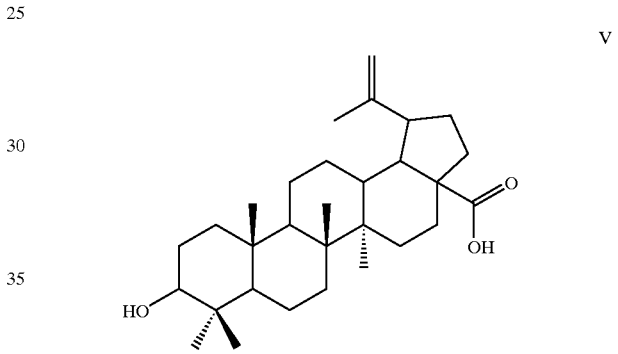

Betulinic aldehyde-3-acetate (VI) (1.455 g, 30.14 mmol) in trifluoromethylbenzene (150 ml) was placed into a round bottom two-neck flask (300 ml). Cobalt (III) acetylacetonate (75 mg, 0.205 mmol) in trifluoromethylbenzene (4 ml) was added to the solution and oxygen was bubbled through the mixture at 60–65° C. for 1 hour. Trifluoromethylbenzene was evaporated under reduced pressure 20 mm Hg, at 40° C.) and sodium hydroxide (0.82 g, 0.0205 mol) in MeOH (100 ml) was added and the mixture boiled for 1.5 hours. Methanol was evaporated under reduced pressure (130 mm Hg, 40° C.), water (150 ml) was added and the mixture was acidified with 15% hydrocloric acid (pH is about 4). The precipitate was filtered and washed with water (3×100 ml). Crystallization from MeOH gives white crystals (1.048 g, 76%) of betulinic acid (V) mp. 290.1–293.4° C. [lit. 291–292], IR (KBr) 3449, 2941, 2869, 1686, 1639, 1451, 1376, 1235, 1186, 1043, 886 cm$^{-1}$; $^1$H NMR (CDCl$_3$), δ 4.79 (S, 1 H, 29 H), 4.65 (S, 1 H, 29 H), 3.22 (DD, 1H, 3-H), 3.02 (T, 1 H, 19H), 1.66 (S, 3 H, 30-Me), 0.79, 0.83, 0.88, 1.0, 1.0 (all S, 5×3 H, 23-, 24-, 25-, 26-, 27-Me), 1.05–2.24 (complex CH—, CH$_2$ 25H); $^{13}$C NMR (CDCl$_3$) δ 180.403, 150.542, 109.86, 79.146, 56.433, 55.471, 50.64, 49.401, 47.025, 42.573, 40.824, 39.01, 38.842, 38.529, 37.348, 37.174, 34.456, 32.291, 30.688, 29.85, 28.138, 27.54, 25.631, 20.982, 19.518, 18.417, 16.282, 15.495, 14.847; MS (E1) of Me-ester: 470, 455, 452, 437, 411, 395, 393, 377, 262, 249, 233, 220, 207, 203, 189, 175, 161, 147, 135, 119, 105, 95, 81, 69, 55, 43.

Example 7

Betulinic acid (V)

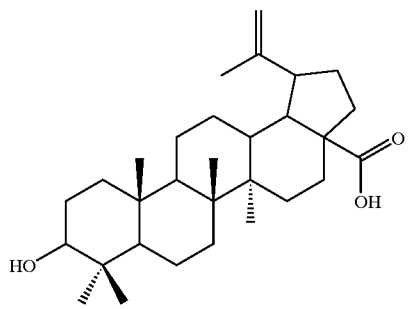

Betulinic acid-3-acetate (IV) (0.5 g, 1.003 mmol) was refluxed in methanol (50 ml) containing sodium hydroxide (0.3 g, 7.5 mmol) for 1 hour. The reaction mixture was then diluted with 100 ml of water and filtered to provide a white residue. The white residue was crystallized (methanol-hexanes) to provide white crystals (0.420 g, 92%) of betulinic acid (V). mp. 290.1–293.4° C. [lit. 291–292], IR (KBr) 3449, 2941, 2869, 1686, 1639, 1451, 1376, 1235, 1186, 1043, 886 cm$^{-1}$; $^1$H NMR (CDCl$_3$), δ 4.79 (S, 1H, 29 H), 4.65 (S, 1 H, 29 H), 3.22 (DD, 1 H, 3-H), 3.02 (T, 1 H, 19 H), 1.66 (S, 3 H, 30-Me), 0.79, 0.83, 0.88, 1.0, 1.0 (all S, 5×3 H, 23-, 24-, 25-, 26-, 27-Me), 1.05–2.24 (complex CH—, CH$_2$ 25 H); $^{13}$C NMR (CDCl$_3$) δ 180.403, 150.542, 109.86, 79.146, 56.433, 55.471, 50.64, 49.401, 47.025, 42.573, 40.824, 39.01, 38.842, 38.529, 37.348, 37.174, 34.456, 32.291, 30.688, 20.85, 28.138, 27.54, 25.631, 20.982, 19.518, 18.417, 16.282, 16.173, 15,495, 14,847; MS (E1) of Me-ester: 470, 455, 452, 437, 411, 395, 393, 377, 262, 249, 233, 220, 207, 203, 189, 175, 161, 147, 135, 119, 105, 95, 81, 69, 55, 43.

Example 8

Betulin 3,28-dibenzoate (II)

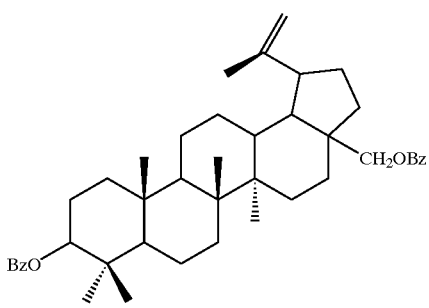

Betulin (I) (2 g, 4.52 mmol), benzoylchloride (1.40 g, 9.96 mmol) and pyridine (25 mL) were introduced into round bottom flask (50 mL). The mixture was maintained at 50–60° C. for 24 hours. The solution was poured into dichloromethane (100 mL) and washed with water (2×50 mL), 1% HCl (50 mL) and water until a neutral reaction of universal indicator paper was observed (i.e., pH=7). Chromatography on a silica column (Ether:Hexane=25:75) yields white crystals (2.41 g) of betulin 3,28-dibenzoate (II): IR (thin layer) 3068, 2946, 2871, 1790, 1716, 1641, 1600,1451, 1315, 1273, 1212, 1174, 1113, 1069, 1015, 710 cm$^{-1}$; $^1$H NMR (CDCl$_3$) δ 8.05 (T, 4 H (D+D), benz. H), 7.58 (T, 2 H, benz. H), 7.43 (T, 4 H (D+D), benz H), 4.73 (DD, 1 H, 3 H), 4.724 (S, 1 H, 29 H), 4.61 (S, 1 H, 29 H), 4.54 (D, 1 H, 28 H, J=11 Hz), 4.1 (D, 1 H, 28 H, J=1 Hz), 2.55 (M, 1 H, 19 H), 1.71 (S, 3 H, 30 Me), 0.9, 0.902, 1.0, 1.02, 1.08 (all S, 5×3 H, 23-, 24-, 25-, 26-, 27-Me), 0.8–2.16 (complex CH—, CH$_2$—, 25 H); $^{13}$C NMR (CDCl$_3$) δ 167.24, 166.58, 150.39, 133.19, 133.02, 130.867, 130.751, 129,867, 128.681, 110.282, 81.856, 68.623, 63.559, 55.74, 55.588, 49.153, 48.103, 47.018, 43.075, 41.232, 38.696, 38.492, 37.953, 37.413, 35.031, 34.419, 30.25, 29.923, 28.421, 27.438, 25.484, 24.064, 22.264, 21.142, 19.473, 18.504, 17.105, 16.493, 16.384, 15.116.

Example 9

Betulin 3-Benzoate (III)

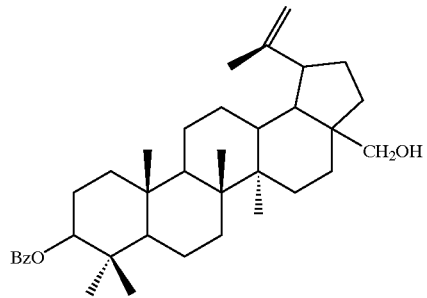

A stirred solution of betulin dibenzoate (II) (1 g, 1.54 mmol) in isopropanol (25 ml) was maintained in a round bottom flask (50 ml). Powdered aluminum isopropoxide (i.e., Al(OiPr)$_3$) (1.56 g, 7.7 mmol) was added and the mixture was refluxed for twenty-four hours. Isopropyl alcohol was distilled under reduced pressure (100 mm Hg) at 30–33° C. The residue was dissolved in dichloromethane (50 ml) and water (2.07 ml) was added to the solution. After stirring (15 minutes) the resulting precipitate was filtered and washed with dichloromethane (4×10 ml) and dried over sodium sulfate (1 g). Solvent evaporation gave white crystals (m=0.81 g, yield 96%) of betulin-3-benzoate (III) IR (KBr) 3496, 2944, 2871, 1715, 1639, 1451, 1390, 1375, 13.15, 1276, 1176, 1116, 1026, 973, 909, 883, 733, 712 cm$^{-1}$; $^1$H NMR (CDCl$_3$) δ 8.04 (D, 2 H, benz. H), 7.57 (T, 1 H, benz. H), 7.42 (T, 2 H, benz. H), 4.72 (DD, 1H, 3-H), 4.70 (S, 1 H, 29-H), 4.58 (S, 1 H, 29-H), 3.80 (D, 1 H, 28-H, J=11 Hz), 3.34 (D, 1 H, 28-H, J=11 Hz), 2.4 (M, 1 H, 19-H), 1.696 (S, 3 H, 30-Me), 0.90, 0.92, 1.003, 1.003, 1.047, (all S, 5×3H, 27-, 23-, 24-, 25-, 26-Me), 0.8–2.1 (complex CH—, CH$_2$ 24 H,); $^{13}$C NMR (CDCl$_3$) δ 166.17, 150.761, 133.0.17, 131.246, 129.818, 128.616, 110.042, 81.878, 60.782, 55.718, 50.588, 49.036, 48.089, 43.024, 41.239, 38.681, 38.492, 37.588, 37.413, 34.455, 34.28, 30.039, 29.463, 28.414, 27.343, 25.463, 24.042, 21.171, 19.386, 18.519, 17.098, 16.5, 16.303, 15.065.

All publications, patents, and patent documents are incorporated by reference herein, as though individually incorporated by reference. The invention has been described with reference to various specific and preferred embodiments and techniques. However, it should be understood that many variations and modifications can be made while remaining within the spirit and scope of the invention.

What is claimed is:

1. A process for preparing a compound of formula III

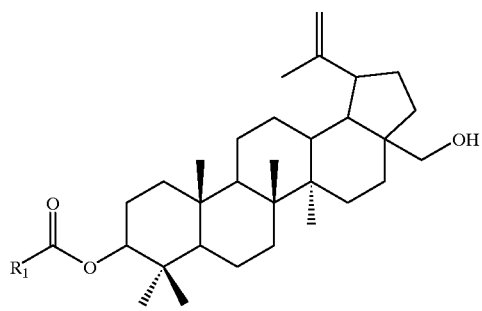

comprising:

(1) acylating a compound of formula I

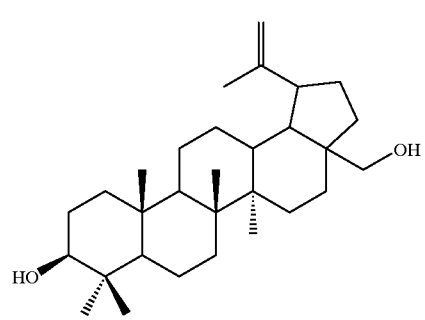

to provide a corresponding compound of formula II

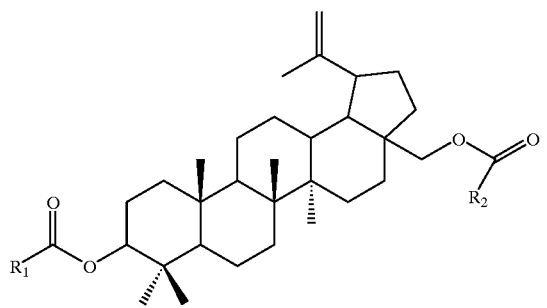

wherein $R_1$ and $R_2$ are each independently any suitable organic group; and (2) alcoholyzing a compound of formula II to provide a corresponding compound of formula III.

2. The process of claim 1 wherein the acylating comprises heating to reflux in acetic acid and acetic anhydride for about 2 hours to about 5 hours.

3. The process of claim 1 wherein the acylating comprises heating in pyridine and benzoyl chloride at about 50° C. to about 60° C. for about 20 hours to about 30 hours.

4. The process of claim 1 wherein the alcoholyzing comprises heating in the presence of an aluminum alkoxide and an anhydrous alcohol.

5. The process of claim 1 wherein $R_1$ and $R_2$ are each $(C_1-C_{10})$alkyl.

6. The process of claim 5 wherein $(C_1-C_{10})$alkyl is methyl.

7. The process of claim 6 wherein the aluminum alkoxide is aluminum isopropoxide.

8. The process of claim 1 wherein the alcohol is isopropanol.

9. The process of claim 1 further comprising oxidizing the compound of formula III to provide a compound of formula VI

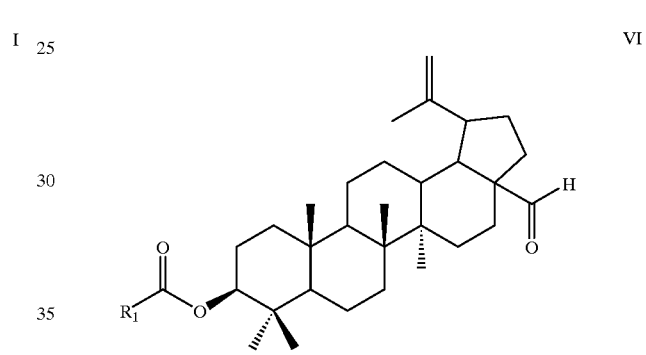

10. The process of claim 9 further comprising oxidizing the compound of formula VI to provide a compound of formula IV

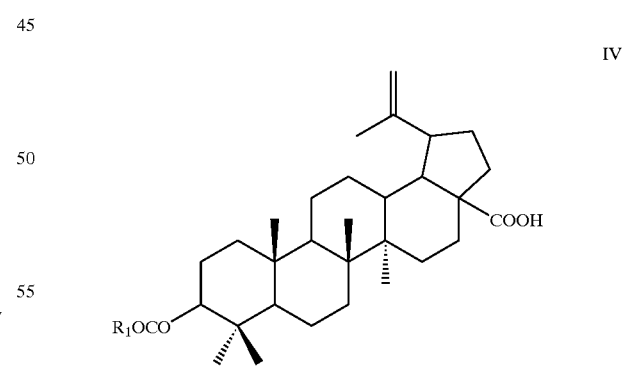

11. The process of claim 10 further comprising deprotecting the compound of formula IV to provide a compound of formula V

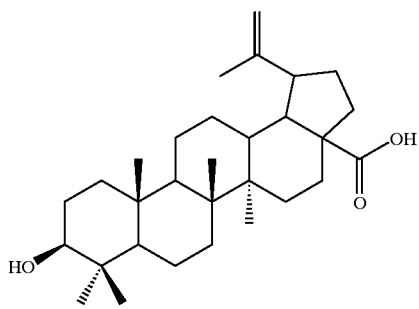

V

12. A process for preparing the compound of formula V

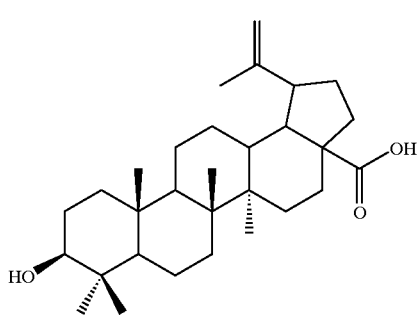

V comprising:

(1) acylating a compound of formula I

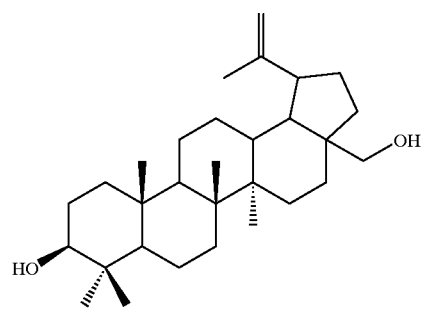

I to provide a corresponding compound of formula II

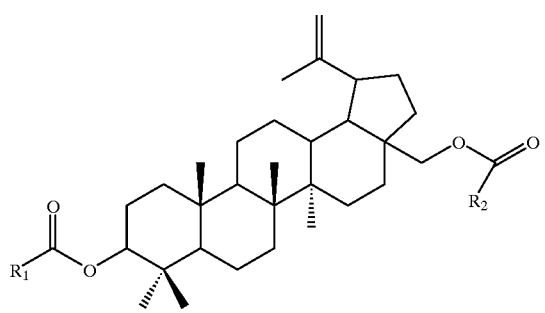

II wherein $R_1$ and $R_2$ are each independently any suitable organic group;

(2) alcoholyzing a compound of formula II to provide a corresponding compound of formula III;

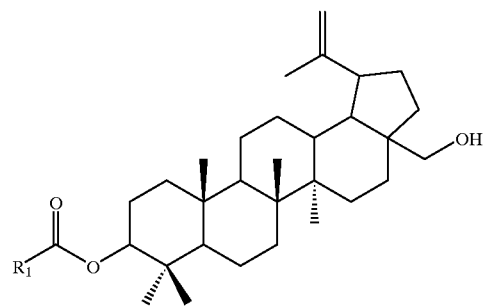

III (3) oxidizing the compound of formula III to provide a corresponding compound of formula VI;

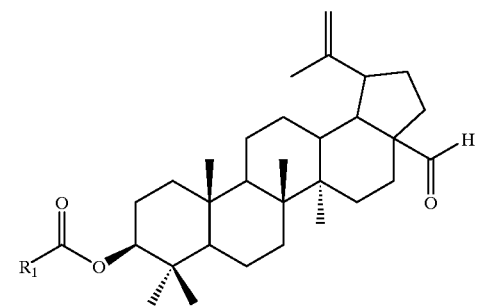

VI (4) oxidizing the compound of formula VI to provide a compound of formula IV; and

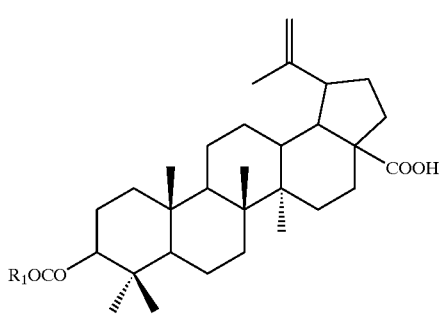

IV (5) deprotecting the compound of formula IV to provide the compound of formula V.

V

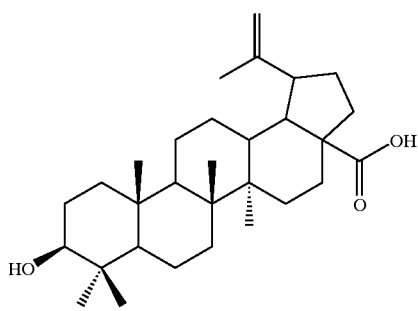

13. The process of claim 12 wherein $R_1$ and $R_2$ are each methyl.

14. The process of claim 12 wherein the alcoholyzing comprises heating the compound of formula II in the presence of an aluminum alkoxide and an anhydrous alcohol.

15. The process of claim 14 wherein the aluminum alkoxide is aluminum isopropoxide.

16. The process of claim 14 wherein the alcohol is isopropanol.

17. The process of claim 12 wherein the acylating comprises heating to reflux in acetic acid and acetic anhydride for about 2 hours to about 5 hours.

18. The process of claim 12 wherein the acylating comprises heating in pyridine and benzoyl chloride at about 50° C. to about 60° C. for about 20 hours to about 30 hours.

19. The process of claim 12 wherein the oxidizing of compound III to compound VI comprises palladium acetate, molecular sieves, and oxygen in trifluoromethylbenzene and pyridine at about 80° C. to about 85° C. for about 0.5 hour to about 4 hours.

20. The process of claim 12 wherein the oxidizing of compound VI to compound IV comprises oxygen and Cobalt (III) acetylacetonate in trifluoromethylbenzene at 60–65° C. for about 0.5 hour to about 2 hours.

21. The process of claim 12 wherein the deprotecting comprises heating to reflux in methanol, water and sodium hydroxide.

22. A process for preparing a compound of formula III

III

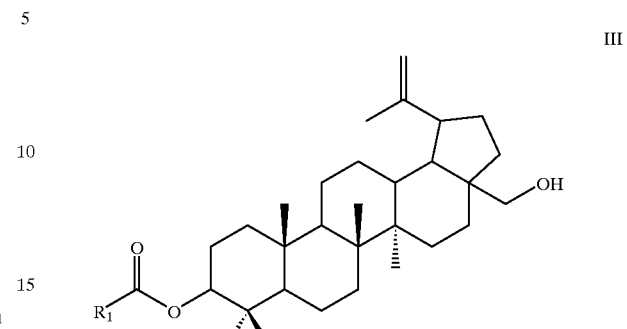

comprising: alcoholyzing a corresponding compound of formula II

II

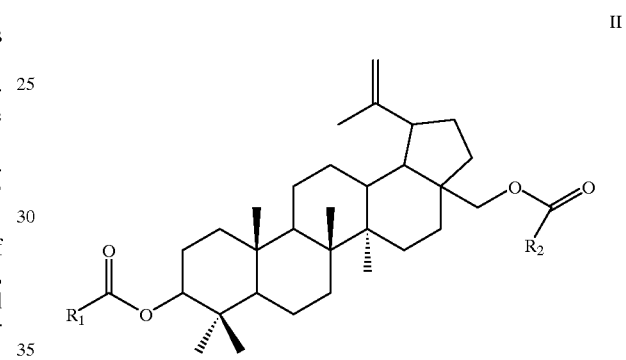

wherein $R_1$ and $R_2$ are each independently any suitable organic group; to provide the compound of formula III.

* * * * *

UNITED STATES PATENT AND TRADEMARK OFFICE
CERTIFICATE OF CORRECTION

PATENT NO.         : 6,232,481 B1                                        Page 1 of 1
APPLICATION NO.    : 09/480406
DATED              : May 15, 2001
INVENTOR(S)        : Pavel A. Krasutsky, Robert M. Carlson and Vitaliy V. Nesterenko It is certified that error appears in the above-identified patent and that said Letters Patent is hereby corrected as shown below:

On The title page (57):
    On line 1, after "preparing" insert --an ester of--
On line 2, after "betulin" delete "-" and insert -- at the --
On line 2, after "3-" delete "acetate" and insert --position, eg.g., betuline-3-acetate, --
On line 2, delete "alcoholyzing" and insert -- the selective alcoholysis of a --
On line 2, after "betulin" insert -- - --
On line 3, delete "dibenzoate;" and insert -- diester, e.g., betulin-3,28-diacetate; --
On line 3, delete "process" and insert -- method --.
On line 4, delete ":"
On line 4, insert after "betuline" -- - --
On line 4, delete "dibenzoate" and insert -- diacetate --
On line 5, delete "alcoholyzing" and insert -- the alcoholysis of --
On line 5, after "betuline" insert -- - --
On line 5, delete "dibenzoate" and insert -- diacetate --
On line 6, delete "process" and insert -- method --
On line 7, delete "including:"
On line 7, after "betulin" insert -- - --
On line 8, delete "dibenzoate" and insert -- diacetate --
On line 8, delete "alcoholyzing" and insert -- the alcoholysis of --
On line 8, after "betulin" insert -- - --
On line 9, after "acetate;" insert -- acetate, --
On line 10, delete "acetate;" and insert -- acetate, --
On line 11, delete "acetate;" and insert -- acetate, --

Signed and Sealed this

Twenty-fourth Day of July, 2007

JON W. DUDAS
*Director of the United States Patent and Trademark Office*